US011229451B2

(12) United States Patent
Guerra et al.

(10) Patent No.: US 11,229,451 B2
(45) Date of Patent: Jan. 25, 2022

(54) THROMBECTOMY CATHETER AND METHODS OF USE

(71) Applicants: Eric Raul Guerra, Ooltewah, TN (US); Xochitl Brahms Guerra, Ooltewah, TN (US); Mayra Paulina Guerra, Ooltewah, TN (US)

(72) Inventors: Eric Raul Guerra, Ooltewah, TN (US); Xochitl Brahms Guerra, Ooltewah, TN (US); Mayra Paulina Guerra, Ooltewah, TN (US)

( * ) Notice: Subject to any disclaimer, the term of this patent is extended or adjusted under 35 U.S.C. 154(b) by 480 days.

(21) Appl. No.: 16/221,471

(22) Filed: Dec. 15, 2018

(65) Prior Publication Data

US 2019/0175209 A1 Jun. 13, 2019

Related U.S. Application Data

(63) Continuation-in-part of application No. 15/964,593, filed on Apr. 27, 2018, now Pat. No. 11,134,967.

(Continued)

(51) Int. Cl.

| | |
|---|---|
| ***A61B 17/221*** | (2006.01) |
| ***A61M 25/00*** | (2006.01) |
| ***A61M 25/09*** | (2006.01) |
| ***A61B 17/3207*** | (2006.01) |
| ***A61B 17/22*** | (2006.01) |

(Continued)

(52) U.S. Cl.

CPC .... *A61B 17/320725* (2013.01); *A61B 17/221* (2013.01); *A61B 17/22031* (2013.01); *A61M 25/007* (2013.01); *A61M 25/0041* (2013.01); *A61M 25/09* (2013.01); *A61B 5/6857* (2013.01); *A61B 2017/2212* (2013.01); *A61B 2017/22039* (2013.01); *A61B 2017/22042* (2013.01); *A61B 2017/22079* (2013.01);

(Continued)

(58) Field of Classification Search

CPC .............. A61B 17/221; A61B 17/3207; A61B 2017/00358; A61B 2017/00331; A61M 25/0074; A61M 25/0905; A61M 25/003; A61M 25/0147; A61M 2025/09175; A61M 2025/0037

See application file for complete search history.

(56) References Cited

U.S. PATENT DOCUMENTS

| | | | |
|---|---|---|---|
| 5,192,286 | A | 3/1993 | Phan et al. |
| 5,720,754 | A | 2/1998 | Middleman et al. |

(Continued)

OTHER PUBLICATIONS

International Search Report and Written Opinion dated Aug. 24, 2018 for corresponding PCT Applicatiton No. PCT/US2018/038446.

*Primary Examiner* — Anh T Dang

(74) *Attorney, Agent, or Firm* — Mathew L. Grell; Grell & Watson Patent Attorneys LLC

(57) ABSTRACT

A thrombectomy catheter with a catheter or delivery sheath having a dual lumen extending therethrough, the catheter having a proximal segment and a distal segment and a linear section coupled therebetween, the distal segment configured as a loop, a port or aperture formed therein said dual lumen of said catheter, the port positioned proximate the distal segment, and a guidewire configured to longitudinally traverse therethrough one of the dual lumen of the catheter, an aspiration device connected thereto one of the dual lumen and configured to create a vacuum therein the catheter and the loop to extract a biomaterial.

22 Claims, 11 Drawing Sheets

Related U.S. Application Data

(60) Provisional application No. 62/598,436, filed on Dec. 13, 2017.

(51) Int. Cl.
*A61B 90/00* (2016.01)
*A61B 5/00* (2006.01)

(52) U.S. Cl.
CPC ............... *A61B 2090/08021* (2016.02); *A61B 2217/005* (2013.01); *A61M 2025/091* (2013.01)

(56) References Cited

U.S. PATENT DOCUMENTS 5,846,260 A 12/1998 Maahs
5,848,964 A 12/1998 Samuels
6,129,739 A 10/2000 Khosravi
6,179,861 B1 1/2001 Khosravi et al.
6,325,815 B1 12/2001 Kusleika et al.
6,530,939 B1 3/2003 Hopkins et al.
6,610,077 B1 8/2003 Hancock et al.
7,410,491 B2 8/2008 Hopkins et al.
7,651,514 B2 1/2010 Salahieh et al.
7,749,220 B2 7/2010 Schmaltz
8,038,674 B2 10/2011 Schmaltz
8,366,737 B2 2/2013 Hancock et al.
9,283,066 B2 3/2016 Hopkins et al.
9,439,664 B2 9/2016 Sos
9,566,412 B2 2/2017 Ulm, III et al.
9,820,764 B2 11/2017 Ulm, III
2002/0045917 A1 4/2002 Ambrisco et al.
2004/0116960 A1 6/2004 Demond et al.
2004/0210194 A1 10/2004 Bonnette et al.
2007/0161963 A1* 7/2007 Smalling ................ A61B 17/22 604/269
2010/0185231 A1 7/2010 Lashinski
2012/0330350 A1 12/2012 Jones et al.
2013/0238009 A9 9/2013 Hopkins et al.
2014/0228869 A1 8/2014 Bonnette et al.
2015/0119853 A1 4/2015 Gainor et al.
2015/0265299 A1 9/2015 Cooper et al.
2016/0038163 A1 2/2016 Thor et al.
2016/0095523 A1 4/2016 Langston
2016/0287844 A1 10/2016 Sachar et al.
2016/0367285 A1 12/2016 Sos
2017/0105742 A1 4/2017 Nishigishi
2017/0246444 A1* 8/2017 Domatch .............. A61M 39/28
2017/0312069 A1 11/2017 Sachar et al.
2017/0340787 A1 11/2017 Corbett et al.

* cited by examiner

THROMBECTOMY CATHETER AND METHODS OF USE

CROSS REFERENCE TO RELATED APPLICATIONS

To the full extent permitted by law, the present United States Continuation-in-Part patent application hereby claims priority to and the full benefit of, U.S. patent application Ser. No. 15/964,593, filed Apr. 27, 2018, which is entitled "Thrombectomy Catheter and Methods of Use," which claims priority to U.S. Provisional Application No. 62/598,436, filed Dec. 13, 2017, which is entitled "X-tractor Thrombectomy Catheter and Methods of Use," which are incorporated herein by reference in their entirety.

TECHNICAL FIELD

The disclosure relates generally to medical catheter devices and more specifically it relates to medical catheter devices with a deployable instrument to remove thrombi (blood clots).

BACKGROUND

A catheter is a medical device or apparatus made from medical grade materials serving a broad range of functions, such as insertion into the body to treat diseases or perform a surgical procedure. Moreover, catheters are often of an elongated form having manipulator means at its distal end and utilized for surgical manipulation of matter in a confined or inaccessible space within a human body or animal. For example, catheters may be utilized to perform suturing, cutting with a knife or scissor action, or by capture and retrieval devices through a small arthroscopic, endoscopic incision, percutaneous, or body aperture.

Furthermore, angioplasty, atherectomy, and deployment of stents and stent-grafts, procedures to treat vascular disease, often dislodge material or plaque from the vessel walls, which may result in the formation of clots or the release of emboli, which enter the bloodstream, and may be large enough to occlude smaller downstream vessels and potentially blocking blood flow to tissue. The result may pose a serious threat to the health or life of a patient if the blockage occurs in critical tissue, such as the heart, lungs, or brain.

One previous approach includes a catheter device having a cannula with an axial bore wherein a remote actuator means on a proximate end activates a sliding elastically deformable loop to extend past the confines of the deployment opening on the distal end thereof to deploy the elastically deformable loop and barrier member attached thereto and attains its deployed configuration. One disadvantage of this approach is that the elastically deformable loop may over expand or linearly expand causing a tear in tissue or a vessel in the deployment area. Another disadvantage of this approach is that the elastically deformable loop may slice or puncture the biopsy, clot, or impaling the vessel wall when the sliding elastically deformable loop is expanded and/or retracted back into the deployment opening. Moreover, such elastically deformable loop is generally incapable of preventing material from escaping from the filter (barrier member) during the process of collapsing and retraction.

Another previous approach includes a catheter device having self-expanding vascular device, such as a support hoop expandable to an articulation region for supporting a sac or mesh filter for filtering or removing matter and capturing emboli from within a vascular system. One disadvantage of this approach is that the mesh filter may degrade flow through the vessel and may result in damage to the downstream cells and tissue normally fed by the blocked vessel. Consequently, it may be difficult or impossible to use such devices in small diameter vessels. Therefore, it is readily apparent that there is a recognizable unmet need for a thrombectomy catheter and methods of use thereof that functions to deploy, scoop, collect, and remove material, plaque, clots, and emboli from the vessel walls without causing a tear in tissue or a vessel, slice or puncture the biopsy, clot, or impale the vessel wall. Also, to prevent material from escaping from the filter (barrier member) during the process of collapsing and retraction, not degrade flow through the vessel and may result in damage to the downstream cells and tissue normally fed by the blocked vessel, and enable operation in small diameter vessels.

SUMMARY

Briefly described, in example embodiment, the present apparatus overcomes the above-mentioned disadvantage, and meets the recognized need for a thrombectomy catheter and methods of use, by providing a catheter or delivery sheath having a dual lumen (passageway) extending therethrough, the catheter having a proximal segment and a distal segment and a linear section coupled therebetween, the distal segment configured as a loop (pigtail) or rim, a port or aperture formed therein said dual lumen of said catheter, the port positioned proximate the distal segment, and a guidewire configured to longitudinally traverse therethrough one of the dual lumen of the catheter, said guidewire configured with a mesh strainer (basket/net) configured to longitudinally traverse therethrough the other of the dual lumen of the catheter and exit therethrough said port and follow said loop to form retractable mesh strainer and, thus, functions to deploy, scoop, collect, and remove material, plaque, clots, and emboli from the vessel interior without causing a tear in tissue or a vessel, slice or puncture the biopsy, clot, or impale the vessel wall, to prevent material from escaping from the filter (barrier member) during the process of collapsing and retraction, not degrade flow through the vessel and may result in damage to the downstream cells and tissue normally fed by the blocked vessel, and enable operation in small diameter vessels.

According to its major aspects and broadly stated, the thrombectomy catheter and methods of use, includes a catheter or delivery sheath having a dual lumen extending therethrough, the catheter having a proximal segment and a distal segment and a linear section coupled therebetween, the distal segment configured as a loop, a port or aperture formed therein said dual lumen of said catheter, the port positioned proximate the distal segment, and a guidewire configured to longitudinally traverse therethrough one of the dual lumen of the catheter, said guidewire having a first end affixed to a mesh strainer, the mesh strainer configured to longitudinally traverse therethrough the other of the dual lumen of the catheter and exit therethrough said port and follow said loop to form retractable mesh strainer.

In an exemplary embodiment of the remotely operated surgical device includes a flexible positioning instrument having an elongated catheter with a dual lumen bore therein extending from a first catheter end to a second catheter end, the dual lumen bore having a first lumen and a second lumen, and a pigtail attached thereto the second catheter end, the first lumen extends therethrough the elongated catheter and the pigtail, the second lumen extends therethrough the elongated catheter, a guidewire extendable therethrough the first lumen of the elongated catheter and the pigtail, and extendable therefrom the pigtail, the guidewire configured to angle the pigtail, and a retraction instrument configured having a proximal member and a distal member coupled to the proximal member, the distal member having a deformable rim and a barrier membrane affixed thereto the deformable rim and extendable therethrough the second lumen of the elongated catheter.

In a further exemplary embodiment of the method for removing a biomaterial from a patient's vessel including the steps of providing a remotely operated surgical device having a flexible positioning instrument, the flexible positioning instrument having an elongated catheter with a dual lumen bore therein extending from a first catheter end to a second catheter end, the dual lumen bore having a first lumen and a second lumen, and a pigtail attached thereto the second catheter end, the first lumen extends therethrough the elongated catheter and the pigtail, the second lumen extends therethrough the elongated catheter, a guidewire extendable therethrough the first lumen of the elongated catheter and the pigtail, and a retraction instrument configured having a proximal member and a distal member coupled to the proximal member, the distal member having a deformable rim and a barrier membrane affixed thereto the deformable rim and extendable therethrough the second lumen of the elongated catheter, maneuvering the operated surgical device therethrough the patient's vessel, positioning the pigtail proximate the biomaterial, deploying the deformable rim and the barrier membrane therefrom the second lumen, rotating the deformable rim and the barrier membrane proximate the biomaterial, collecting the biomaterial therein the barrier membrane, retracting the deformable rim, the barrier membrane, and the biomaterial therethrough the second lumen.

Accordingly, a feature of the thrombectomy catheter and methods of use is its ability to spin the pigtail or distal segment configured as a loop multiple times proximate the undesirable material enabling it to scoop up clots, plaque, emboli, thrombi (blood clots), fatty deposit, or other undesirable material or debris therein mesh blood strainer and extract them from a human blood vessel.

Another feature of the thrombectomy catheter and methods of use is its ability to provide a mesh strainer or basket porous so that blood cells may pass through freely while clots, plaque, emboli, thrombi (blood clots), fatty deposit, or other undesirable material or debris are captured therein.

Still another feature of the thrombectomy catheter and methods of use is its ability to provide a dual lumen catheter where one lumen forms a passageway for the guidewire and the other lumen forms a passageway for the mesh strainer.

Yet another feature of the thrombectomy catheter and methods of use is the ability to provide a remotely operable surgical device or guidewire.

Yet another feature of the thrombectomy catheter and methods of use is the ability to provide a flexible a dual lumen catheter.

Yet another feature of the thrombectomy catheter and methods of use is the ability to provide a flexible a dual lumen catheter having a flexible pigtail having a passageway for the guidewire and a deployment or exit port formed proximate or at the tip end.

Yet another feature of the thrombectomy catheter and methods of use is the ability to provide a retractable mesh strainer that traverses therearound the distal segment configured as a loop to form a basket or net to scoop up clots, plaque, emboli, or other dislodge matter therein mesh strainer.

Yet another feature of the thrombectomy catheter and methods of use is the ability to provide a catheter with a deployable mesh basket, net, mesh strainer to track around a loop, pigtail on the distal segment of the catheter.

Yet another feature of the thrombectomy catheter and methods of use is the ability to provide a vascular device that overcomes disadvantages of previously known vascular filter nets and thrombectomy/embolectomy devices, and employs few components.

Yet another feature of the thrombectomy catheter and methods of use is the ability to provide a vascular device that is capable of being contracted to a small delivery profile, thus permitting use of the device in small blood vessels.

Yet another feature of the thrombectomy catheter and methods of use is the ability to provide a vascular device without the need for specialized delivery catheters.

Yet another feature of the thrombectomy catheter and methods of use is the ability to provide a vascular device to provide a vascular device that reduces the risk of clots, plaque, emboli, thrombi (blood clots), fatty deposit, or other undesirable material or debris escaping from the device when the device is retracted and removed.

Yet another feature of the thrombectomy catheter and methods of use is the ability to provide a vascular device to percutaneously remove clots, plaque, emboli, thrombi (blood clots), fatty deposit, or other undesirable material or debris from human blood vessel without performing surgery or without giving a clot buster.

Yet another feature of the thrombectomy catheter and methods of use is the ability to provide a vascular device to capture clots, plaque, emboli, thrombi (blood clots), fatty deposit, or other undesirable material or debris from human blood vessel just by spinning the pigtail, loop, or distal segment configured as a loop multiple times proximate the undesirable material.

Yet another feature of the thrombectomy catheter and methods of use is the ability to remove the net, basket, deployable mesh basket, or mesh strainer multiple times through the dual lumen catheter without losing position of the pigtail, loop, or distal segment configured as a loop adjacent to the working area.

Yet another feature of the thrombectomy catheter and methods of use is the ability to provide a vascular device with aspiration or suction via an aspiration device to collect and remove clots, plaque, emboli, thrombi (blood clots), fatty deposit, or other undesirable material or debris from human blood vessel by suctioning undesirable material (aspiration thrombectomy) therein a distal end of a lumen proximate the undesirable material and drawing such down the lumen channel.

These and other features of the thrombectomy catheter and methods of use will become more apparent to one skilled in the art from the following Detailed Description of the Embodiments and Claims when read in light of the accompanying drawing Figures.

BRIEF DESCRIPTION OF THE DRAWINGS

The present thrombectomy catheter and methods of use will be better understood by reading the Detailed Description of the embodiments with reference to the accompanying drawing figures, in which like reference numerals denote similar structure and refer to like elements throughout, and in which:

FIG. 1B is a perspective cross-sectional view of an exemplary embodiment of a dual lumen elongated catheter of the thrombectomy catheter of FIG. 1A;

FIG. 1C is a perspective cross-sectional view of an exemplary embodiment of a single lumen pigtail of the thrombectomy catheter of FIG. 1A;

It is to be noted that the drawings presented are intended solely for the purpose of illustration and that they are, therefore, neither desired nor intended to limit the disclosure to any or all of the exact details of construction shown, except insofar as they may be deemed essential to the claimed invention.

DETAILED DESCRIPTION

In describing the exemplary embodiments of the present disclosure, as illustrated in FIGS. 1A, 1B, 1C, 2, 3, 4A, 4B, 5A, 5B, 6 7, 8, 9, and 10 specific terminology is employed for the sake of clarity. The present disclosure, however, is not intended to be limited to the specific terminology so selected, and it is to be understood that each specific element includes all technical equivalents that operate in a similar manner to accomplish similar functions. Embodiments of the claims may, however, be embodied in many different forms and should not be construed to be limited to the embodiments set forth herein. The examples set forth herein are non-limiting examples, and are merely examples among other possible examples.

Figure 1A:
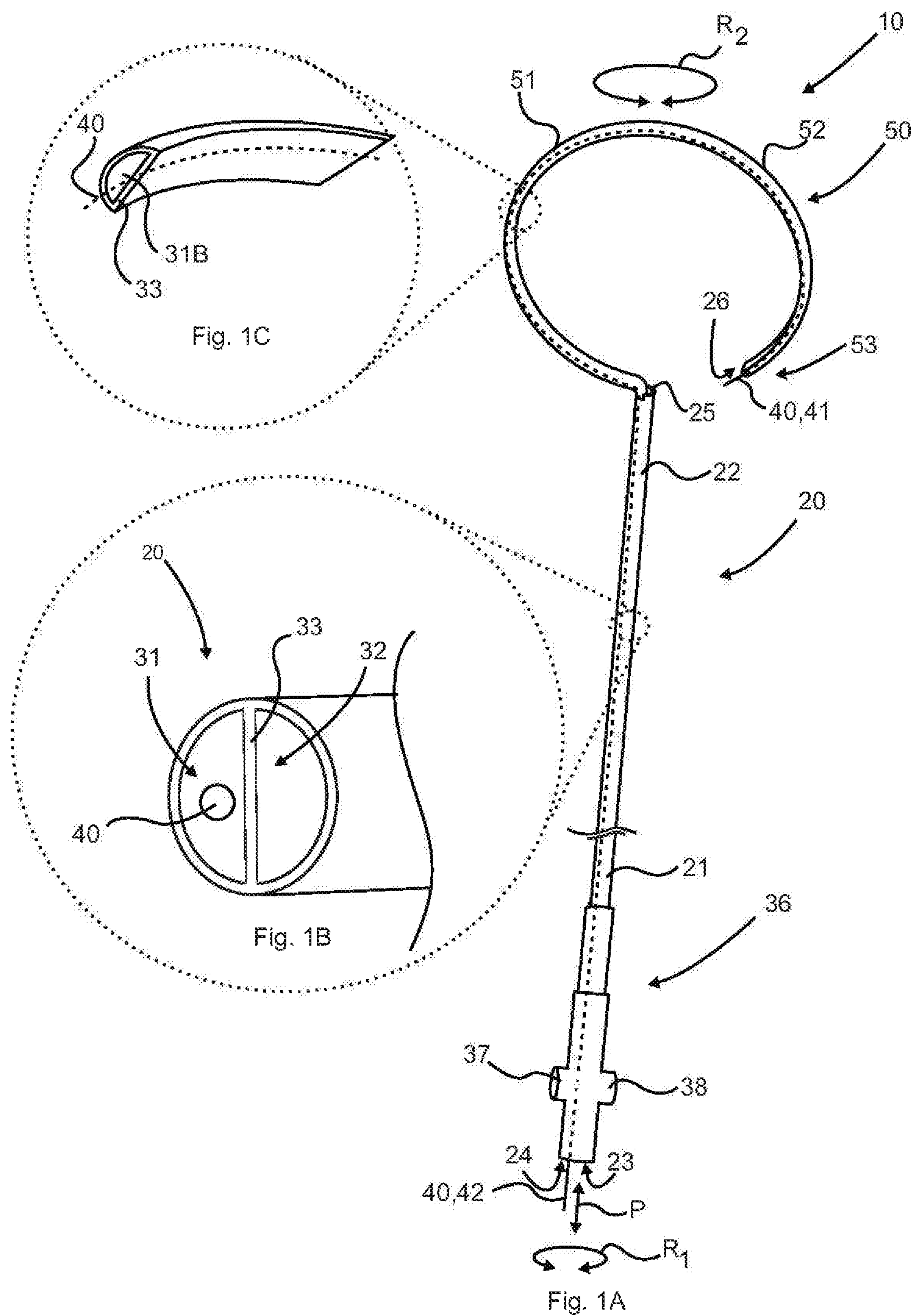
FIG. 1A is a top perspective view of an exemplary embodiment of a thrombectomy catheter.

Referring now to FIGS. 1A, 1B, 1C, by way of example, and not limitation, there is illustrated an example embodiment of a flexible surgical positioning instrument 10. Surgical positioning instrument 10 may include a base section, such as hand grip 36, having first rotation flap 37 and second rotation flap 38, as coupled to a longitudinal linear member, cannula, housing, catheter, or sheath, such as elongated catheter 20 extending linearly therefrom hand grip 36. Preferably, elongated catheter 20 may include two or dual axial bores therethrough or space created inside elongated catheter 20 and extending from first catheter end 21 to second catheter end 22. Moreover, two or dual axial bores therethrough may include first lumen 31 and second lumen 32 separated by divider 33.

Furthermore, second catheter end 22 of surgical positioning instrument 10 may be configured as a loop, open ended loop, or enclosure, such as pigtail 50 formed thereon or attached thereto second catheter end 22. It is contemplated herein that pigtail 50 may be formed in a variety of sizes and configurations and include first pigtail section 51 and second pigtail section 52 with first pigtail section 51 affixed thereto second catheter end 22 of elongated catheter 20 and second pigtail section 52 forming an enclosure that loops around back to a position proximate second catheter end 22. It is contemplated herein that elongated catheter 20 and pigtail 50 may preferably be configured or constructed of plastic, polymeric material includes polytetrafluorethylene, polyurethane, polyethylene, Teflon, and the like as such materials offers a variety of forms, shapes, ease of manufacture, and flexibility; however, other suitable materials may be utilized provided such material has sufficient strength, flexibility, and/or durability as would meet the purpose described herein. The material of elongated catheter 20, second lumen 32 pigtail 50, second lumen or medical instrument exit aperture 25 may be reinforced with fibers, rings, or longitudinal ribs, for example, to enable it to withstand the forces exerted on it by retractable instrument 60 while it is constrained within second lumen 32 and deformed by elongated catheter 20.

First lumen 31 may extend therethrough hand grip 36, elongated catheter 20, and pigtail 50, beginning with an entrance hole, such as first lumen or guidewire entrance aperture 24 and exit therefrom pigtail 50 proximate pigtail end 53 through an exit or deployment hole opening to the environment, such as first lumen or guidewire exit aperture 26.

Second lumen 32 may extend therethrough hand grip 36 and elongated catheter 20 beginning with an entrance hole, such as first instrument aperture 23 and exit therefrom elongated catheter 20 proximate second catheter end 22 through an exit or deployment hole, such as second instrument aperture 25 proximate second catheter end 22.

Figure 2:
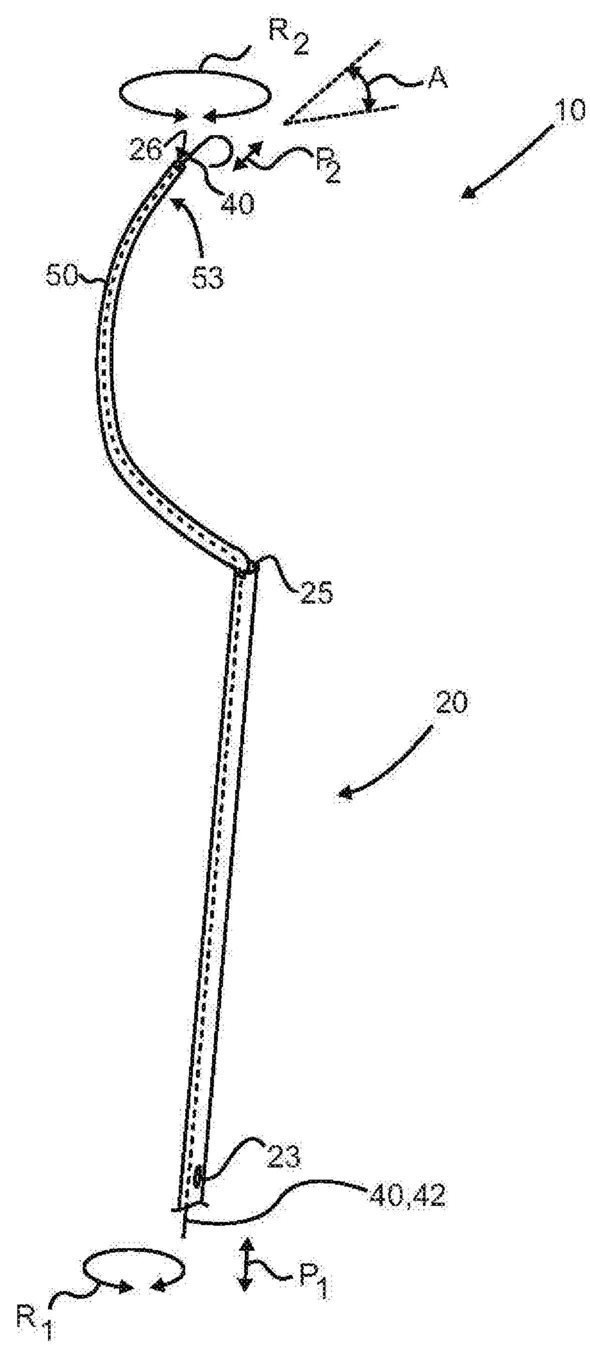
FIG. 2 is a top perspective view of an exemplary embodiment of the thrombectomy catheter of FIG. 1A, shown with a guidewire passing therein a first lumen elongating the pigtail.

Referring now to FIG. 2, by way of example, and not limitation, there is illustrated an example embodiment of guidewire 40 for deployment and retraction use therein first lumen 31 of elongated catheter 20 and pigtail lumen 31B of pigtail 50. Guidewire 40 may include first guidewire end 41 and second guidewire end 42. In use, a path or vessel guiding device, such as guidewire 40 may be extended therethrough first lumen 31 of elongated catheter 20 and pigtail lumen 31B of pigtail 50 beginning with an entrance hole, such as first lumen entrance aperture 24 and exiting therefrom pigtail 50 proximate pig tail end 53 through an exit or deployment hole opening to the environment, such as first lumen exit aperture 26 to a position beyond or extend and extendable therefrom pigtail 50 to assist or guide second catheter end 22 and pigtail 50 therethrough a blood vessel V, turn, fork or other vascular maneuverability. First guidewire end 41 extends through the deployment opening, such as guide wire aperture 26 and is remotely controlled from second guidewire end 42. Moreover, as guidewire 40 passes therethrough pigtail 50, pigtail 50 may angled or straighten (as shown in FIG. 2) or angle, such as pigtail angle A (from approximately 0-270 degrees relative to perpendicular thereto elongated catheter 20, 9 o'clock counterclockwise to 12 o'clock), depending on the flexibility or rigidity of first guidewire end 41 passing therethrough. Furthermore, first rotation R1 of elongated catheter 20 causes or results in similar rotation, such as rotation R2 of pigtail 50. Both pigtail angle A and rotation R2 enable a variety of positions of first guidewire end 41 to assist or guide or position guidewire 40, pigtail 50, and second catheter end 22 therethrough a blood vessel V, turn, fork or other vascular maneuverability. Still furthermore, movement of or moving guidewire 40, such as push/pull P1 of second guidewire end 42 causes first guidewire end 41 to move in and out therefrom guide wire aperture 26 to assist or guide or position guidewire 40, pigtail 50, and second catheter end 22 therethrough a blood vessel, turn, fork or other vascular V maneuverability.

Alternatively, first lumen 31 and pigtail lumen 31B may be utilized as an access for additional laparoscopic or endoscopic devices, and/or fluid access or withdrawal, lighting, video, and like medical instruments 40A. Such an endoscope can also provide surgical implements such as lasers, scalpels, irrigation and aspiration means, visualization means, and the like 40A. The specific configuration and dimensions of first lumen 31 and pigtail lumen 31B will vary with the intended use of surgical positioning instrument 10, and whether access for additional medical instruments 40A is provided. In general the axial bore of first lumen 31 may have an internal diameter of 6-12 F (French=⅓ mm), however other diameters are contemplated herein to accommodate a working channel of an endoscope.

Figure 3:
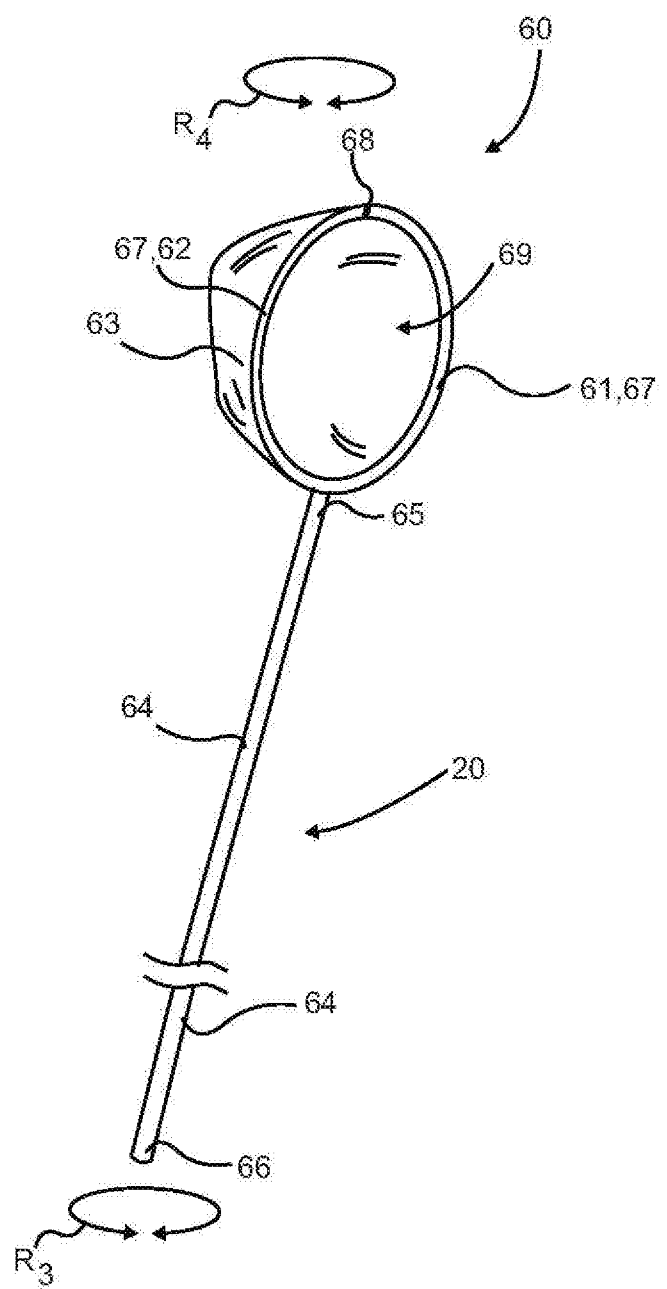
FIG. 3 is a top perspective view of an exemplary embodiment of vascular medical instrument.

Referring now to FIG. 3, by way of example, and not limitation, there is illustrated an example embodiment of a retractable instrument 60, for use with surgical positioning instrument 10. Retractable instrument 60 may include a proximal or elongated member or operator, such as proximal member 64 having a first member end 65 and a second member end 66. First member end 65 may be configured having a loop, enclosure, or basket, pigtail such as deformable rim 67 configured thereon and proximate second member end 66. It is contemplated herein that deformable rim 67 may be configured in a variety of sizes and shapes preferably matching pigtail 50 in size and shape.

Moreover, deformable rim 67 may be configured of one or two components, such as first deformable section 61 and second deformable section 62 and may alternatively include one or more pivot joint 68 therebetween first deformable section 61 and second deformable section 62. Deformable rim 67 is preferably made of a flexible, elastic, or shape memory material or alloy biocompatible material capable of flexing, bending, or collapsing to a configuration which may enter and exit first instrument aperture 23, traverse axial bore of second lumen 32, expanding to deployed net after passing therethrough second instrument aperture 26, and collapsing to re-enter second instrument aperture 26 to extract biomaterial therefrom a blood vessel or other vascular channel or conduit V.

It is further contemplated herein that deformable rim 67 may include one or more joints or hinges, such as pivot point 68 positioned therearound deformable rim 67 or between first deformable section 61 and second deformable section 62 to enable deformable rim 67, first deformable section 61, and second deformable section 62 to linearly collapse or fold and traverse therethrough first instrument aperture 23, axial bore of second lumen 32, and second instrument aperture 25. It is still further contemplated herein that deformable rim 67 may form an opening, such as rim inlet 69.

When expanded, deformable rim 67 may have a diameter of from about 1 cm or less to about 3 cm but other sizes are contemplated herein. Moreover, a barrier membrane or other sifting or filtering membrane, such as mesh strainer 63 preferably runs, spans, or is affixed thereto deformable rim 67 loosely, forming a rounded open end capture net across rim inlet 69. Mesh strainer 63 may be utilized to filter or capture clots, plaque, emboli, thrombi (blood clots), fatty deposit, or other undesirable material or debris from within human blood vessels V.

The specific configuration and dimensions of axial bore of second lumen 32 will vary with the use of surgical positioning instrument 10, the parameters of retractable instrument 60, such as insertion/retraction member 64 and sized to receive deformable rim 67 having first deformable section 61 and second deformable section 62 in a constrained configuration with mesh strainer 63 furled around first deformable section 61, second deformable section 62, and insertion/retraction member 64. In general, the axial bore of second lumen 32 may have an axial bore or internal diameter of 6-12 F (French=⅓ mm) to accommodate retractable instrument 60 in a constrained configuration, however other diameters are contemplated herein.

Alternatively, second lumen 32 may be utilized as an access for additional laparoscopic or endoscopic devices, and/or fluid access or withdrawal, lighting, video, and like medical instruments 40A. Such an endoscope can also provide surgical implements such as lasers, scalpels, irrigation and aspiration means, visualization means, and the like 40A.

Referring again to FIG. 1A, the outer diameter of the catheter 20 may vary with the application, the size of first lumen 31 and second lumen 32, the size of deformable rim 67 of retractable instrument 60 having first deformable section 61 and second deformable section 62, whether access for additional laparoscopic or endoscopic devices, and/or fluid access or withdrawal, lighting, video, and the like 40A, and whether additional lumens are included in surgical positioning instrument 10.

Figures 4A, 4B:
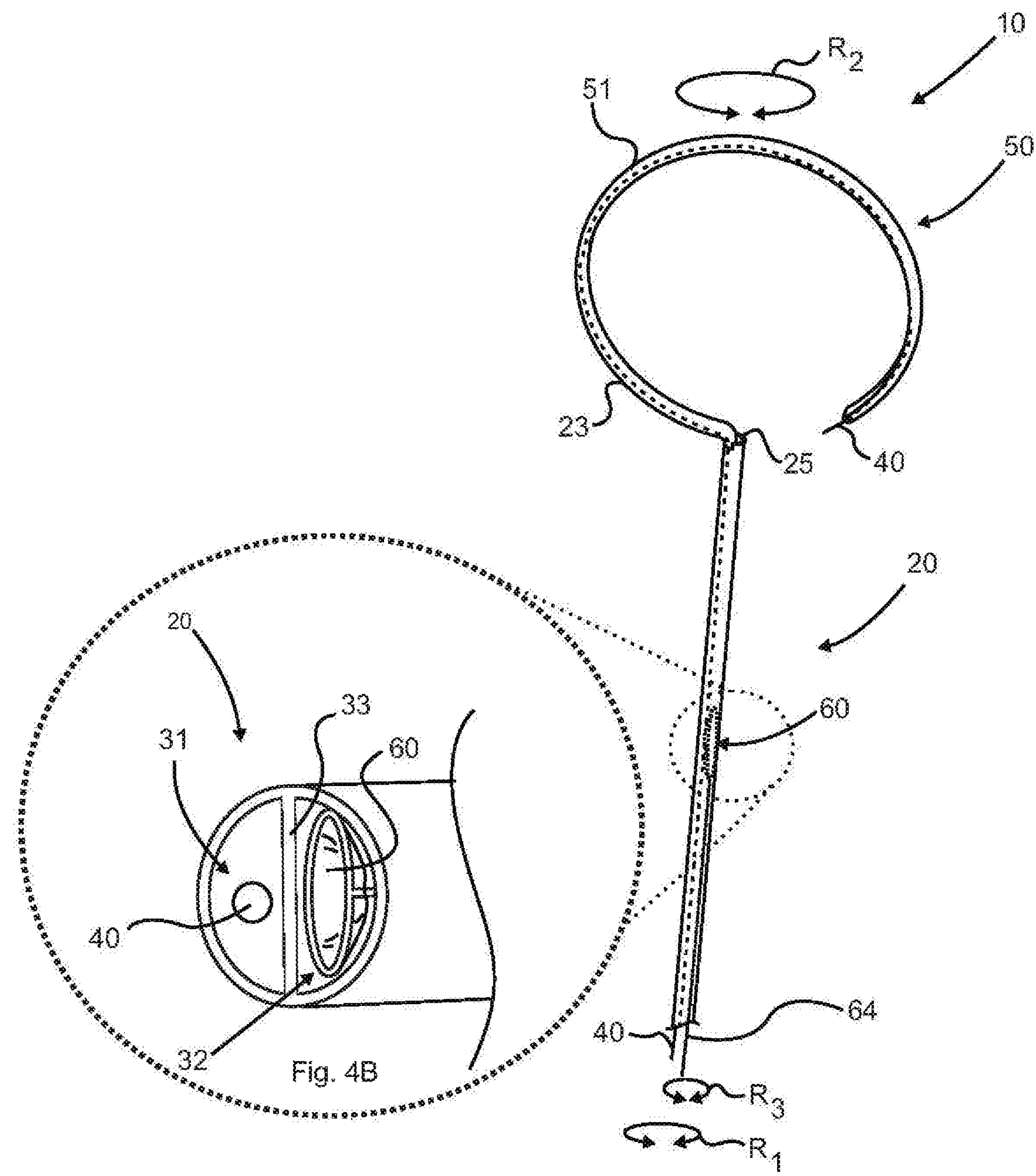
FIG. 4A is a top perspective view of an exemplary embodiment of a thrombectomy catheter of FIG. 1, shown with a guidewire traversing therein first lumen, and retractable instrument traversing therein second lumen.
FIG. 4B is a perspective cross-sectional view of the elongated catheter of a thrombectomy catheter of FIG. 1, shown with a guidewire and a retractable instrument traversing therethrough.

Referring now to FIGS. 4A and 4B, by way of example, and not limitation, there is illustrated an example embodiment of retractable instrument 60 for deployment and retraction use therein second lumen 32 of surgical positioning instrument 10. Moreover, second guidewire end 42 may be pulled and as guidewire 40 retracts therethrough pigtail 50, pigtail 50 may return to pigtail or loop configuration as shown in FIGS. 1 and 4A.

In use, deformable rim 67 of first member end 65 may be preferably collapsed and mesh strainer 63 may be furled or wrapped therearound deformable rim 67 and/or first member end 65 of retractable instrument 60. Collapsed deformable rim 67 and furled mesh strainer 63 may be inserted therein first instrument aperture 23 of second lumen 32. Collapsed deformable rim 67 and furled mesh strainer 63 may be disposed within, extended, and traverse therethrough second lumen 32 of elongated catheter 20 and exit or deploy therethrough or extendable therefrom. Upon deformable rim 67 and furled mesh strainer 63 exit thereof second lumen 32, deformable rim 67 expands to deployed deformable rim 67 with mesh strainer 63 unfurled to an expanded collection state positioned proximate pigtail 50. When deployed first deformable section 61 and second deformable section 62 of deformable rim 67 expand back to a non-compressed position as shown in FIG. 5 to create expanded deformable rim 67 having rim inlet 69 and mesh strainer 63, where expanded deformable rim 67 preferably mates up with or may be positioned proximate or within pigtail 50, as shown in FIG. 5.

Figure 5A:
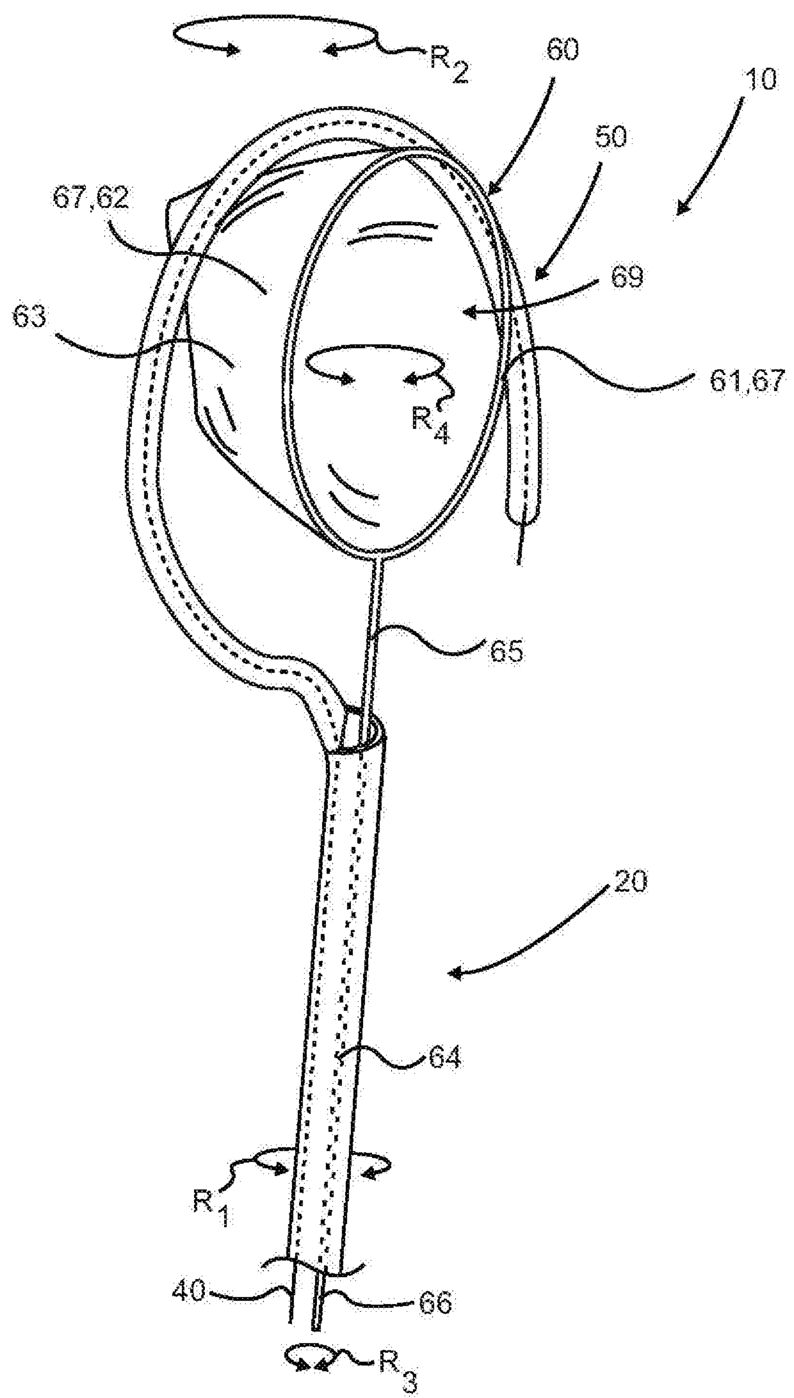
FIG. 5A is a top perspective view of an exemplary thrombectomy catheter of FIG. 1 with retractable instrument deployed therebetween pigtail.
Figure 5B:
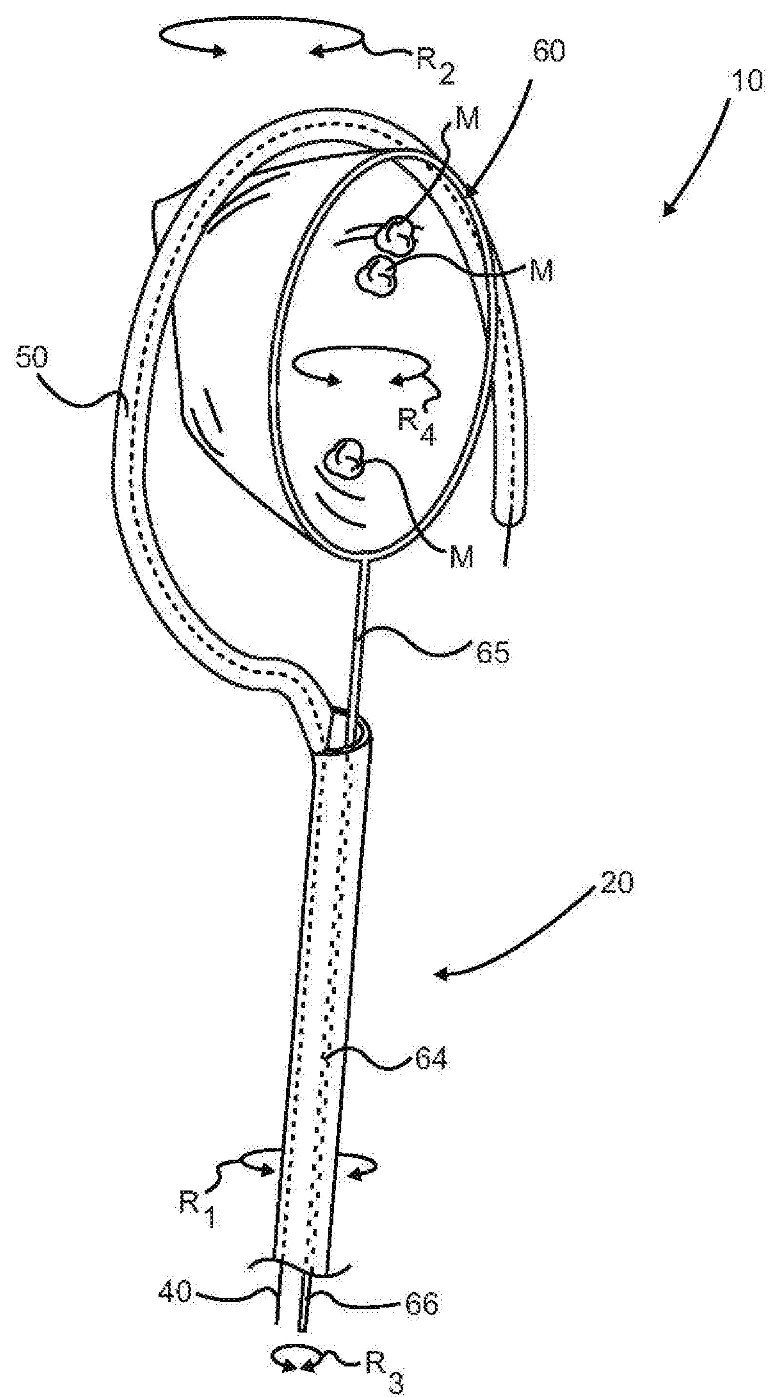
FIG. 5B is a front perspective view of thrombectomy catheter of FIG. 5A with vascular medical instrument, shown netting undesirable material or debris for retrieval.

Referring now to FIGS. 5A and 5B, by way of example, and not limitation, there is illustrated an example embodiment of retractable instrument 60 shown deployed therefrom second lumen 32 of surgical positioning instrument 103 In use, push/pull P1 of second member end 66 may deploy or extend deformable rim 67 within pigtail 50 or past the confines of second instrument aperture 25 on the distal end thereof second catheter end 22 to deploy deformable rim 67 and mesh strainer 63 attached thereto and attains its deployed configuration. Rotation R3 of second member end 66 causes or results in similar rotation, such as rotation R4 of deformable rim 67 having rim inlet 69 and mesh strainer 63, which in turn causes deformable rim 67 having rim inlet 69 and mesh strainer 63 of retractable instrument 60 to scoop up or collect or capture clots, plaque, emboli, thrombi (blood clots), fatty deposit, biomaterial, or other undesirable material or debris M from blood vessel V. Moreover, rotation R1 of elongated catheter 20 results in rotation R2 of pigtail 50 which in turn results in rotation R4 of deformable rim 67 having rim inlet 69 and mesh strainer 63 due to abutting or contact therebetween pigtail 50 and deformable rim 67 (deformable rim 67 abuts pigtail 50), which in turn causes deformable rim 67 having rim inlet 69 and mesh strainer 63 of retractable instrument 60 to scoop up or collect or capture clots, plaque, emboli, thrombi (blood clots), fatty deposit, biomaterial, or other undesirable material or debris M from blood vessel V. Undesirable material or debris M may be removed from blood vessel V by extracting retractable instrument 60 and deformable rim 67 having rim inlet 69 and mesh strainer 63 containing undesirable material or debris M back therein second instrument aperture 25 collapsing deformable rim 67 and pulling retractable instrument 60 down second lumen 32 of surgical positioning instrument 10 and out first instrument aperture 23, as shown in FIGS. 4A and 4B. Push/pull P1 of second member end 66 may retrieve deformable rim 67 by collapsing deformable rim 67 and mesh strainer 63 may be furled or wrapped therearound deformable rim 67 and/or first member end 65, and retractable instrument 60 with undesirable material or debris M may be pulled therethrough second instrument aperture 25 and exit out first instrument aperture 23.

It is contemplated herein that deformable rim 67 and pigtail 50 may be similar or matched in size and shape, such as circumference and/or diameter, to enable abutting or contact therebetween pigtail 50 and deformable rim 67 (deformable rim 67 abuts pigtail 50).

Figure 6:
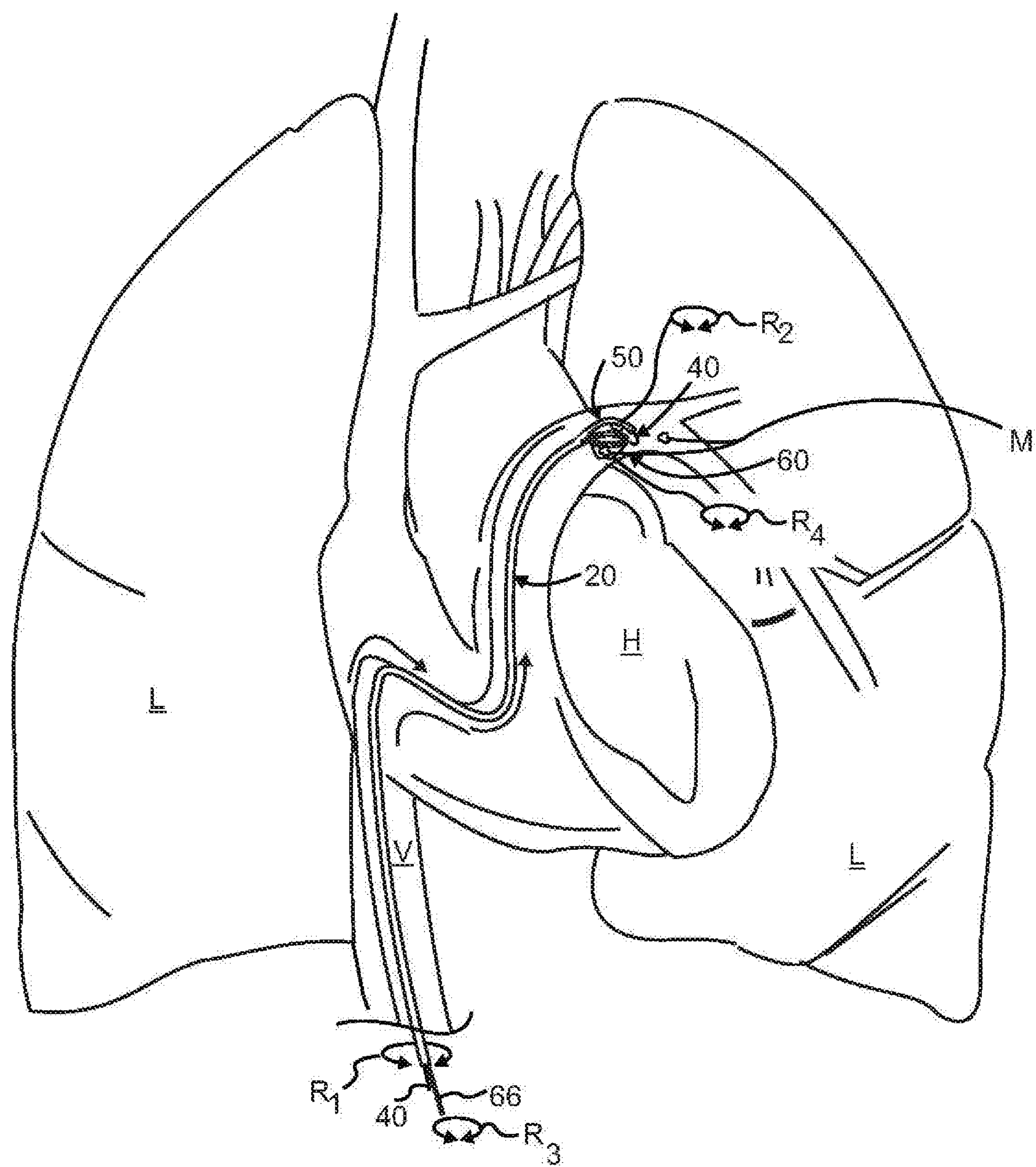
FIG. 6 is a top view of thrombectomy catheter of FIG. 5A passing through the heart and deployed in a vascular vessel of the lung with retractable instrument shown netting undesirable material or debris for retrieval.

Referring now to FIG. 6, by way of example, and not limitation, there is illustrated an example embodiment of surgical device, the combination of retractable instrument 60 and surgical positioning instrument 10. In use, surgical positioning instrument 10, shown with pigtail 50 inserted into a patient and serpentinely deployed therethrough blood vessel V, heart H, lung L, and into lung blood vessel V. It is contemplated herein that surgical positioning instrument 10 may be deployed therein any fluid-carrying vessels where debris needs to be removed.

In use, push/pull P1 of guidewire 40 may be extended therethrough pigtail 50, causing pigtail 50 to straighten or elongate (as shown in FIG. 2) or angle, such as pigtail angle A, therein blood vessel V depending on the flexibility or rigidity of first guidewire end 41 passing therethrough. Furthermore, first rotation R1 of elongated catheter 20 causes pigtail 50 to similarly rotate, rotation R2 therein blood vessel V. Both pigtail angle A and rotation R2 enable a variety of positions of first guidewire end 41 to assist or guide or position guidewire 40, pigtail 50, and second catheter end 22 therethrough or therein blood vessel V, heart H, lung L to serpentine, turn, maneuver a fork of or other vascular maneuverability to precisely maneuver and position pigtail 50 therein blood vessel V. The objective of surgical positioning instrument 10 is to preferably position pigtail 50 in a specific location within a patient's vessel.

Push/pull P1 of second member end 66 results in exit or deployment of deformable rim 67 having rim inlet 69 and mesh strainer 63 therethrough second instrument aperture 25 proximate a junction between second catheter end 22, and expanding to deployed deformable rim 67 with mesh strainer 63 after passing therethrough second instrument aperture 25 to a position proximate pigtail 50 therein blood vessel V.

Moreover, rotation R3 of second member end 66 results in rotation R4 of deformable rim 67 within blood vessel V having rim inlet 69 and mesh strainer 63, which in turn causes deformable rim 67 having rim inlet 69 and mesh strainer 63 of retractable instrument 60 to scoop up or collect or capture clots, plaque, emboli, thrombi (blood clots), fatty deposit, biomaterial, or other undesirable material or debris M from blood vessel V.

Furthermore, rotation R1 of elongated catheter 20 results in rotation R2 of pigtail 50 within blood vessel V which in turn results in rotation R4 of deformable rim 67 having rim inlet 69 and mesh strainer 63 due to abutting or contact therebetween pigtail 50 and deformable rim 67, which in turn causes deformable rim 67 having rim inlet 69 and mesh strainer 63 of retractable instrument 60 to scoop up or collect or capture clots, plaque, emboli, thrombi (blood clots), fatty deposit, biomaterial, or other undesirable material or debris M from blood vessel V.

Push/pull P1 of second member end 66 results in collapsed deformable rim 67 having rim inlet 69 and mesh strainer 63 being retracted or entry therein second instrument aperture 25 and traversing therethrough second lumen 32 to first instrument aperture 23 to remove undesirable material or debris M captured therein mesh strainer 63 from blood vessel V. It is contemplated herein that such capture and retrieval of undesirable material or debris M may be accomplished multiple times with multiple passes, deployment, retract, and retrieval of retractable instrument 60 therethrough second lumen 32 of surgical positioning instrument 10.

It is contemplated herein that second lumen 32 angioplasty, atherectomy, and deployment of stents and stent-grafts, procedures to treat vascular disease may be deployed therethrough second lumen 32. Such instruments often dislodge material or plaque from the vessel walls of blood vessel V, which may result in the formation of clots or the release of emboli, biomaterial, such as undesirable material or debris M, which enter the bloodstream, and may be large enough to occlude smaller downstream vessels and potentially blocking blood flow to tissue. The result may pose a serious threat to the health or life of a patient if the blockage occurs in critical tissue, such as the heart, lungs, or brain. Retractable instrument 60 may be utilized herein to traverse second lumen 32 to capture and remove undesirable material or debris M from blood vessel V.

It is further contemplated herein that pigtail 50 encircling of deformable rim 67 may protect blood vessel V when deformable rim 67 expands preventing contact therewith blood vessel V preventing a tear in tissue or a vessel in the deployment area.

It is still further contemplated herein that pigtail 50 encircling of deformable rim 67 may protect blood vessel V when deformable rim 67 expands or retracts preventing contact therewith blood vessel V preventing slice or puncture the biopsy, clot, or impaling the vessel wall of blood vessel V.

It is yet further contemplated herein that second lumen 32 may be utilized for delivery of other medical instrument(s), such as a suture to conduct a biopsy or other medical instrument to meet the needs of the medical application being performed with surgical positioning instrument 10.

It is yet further contemplated herein that second lumen 32 may be sized or configured adjustable to accommodate different diameter or sized medical instruments 60.

Figure 7:
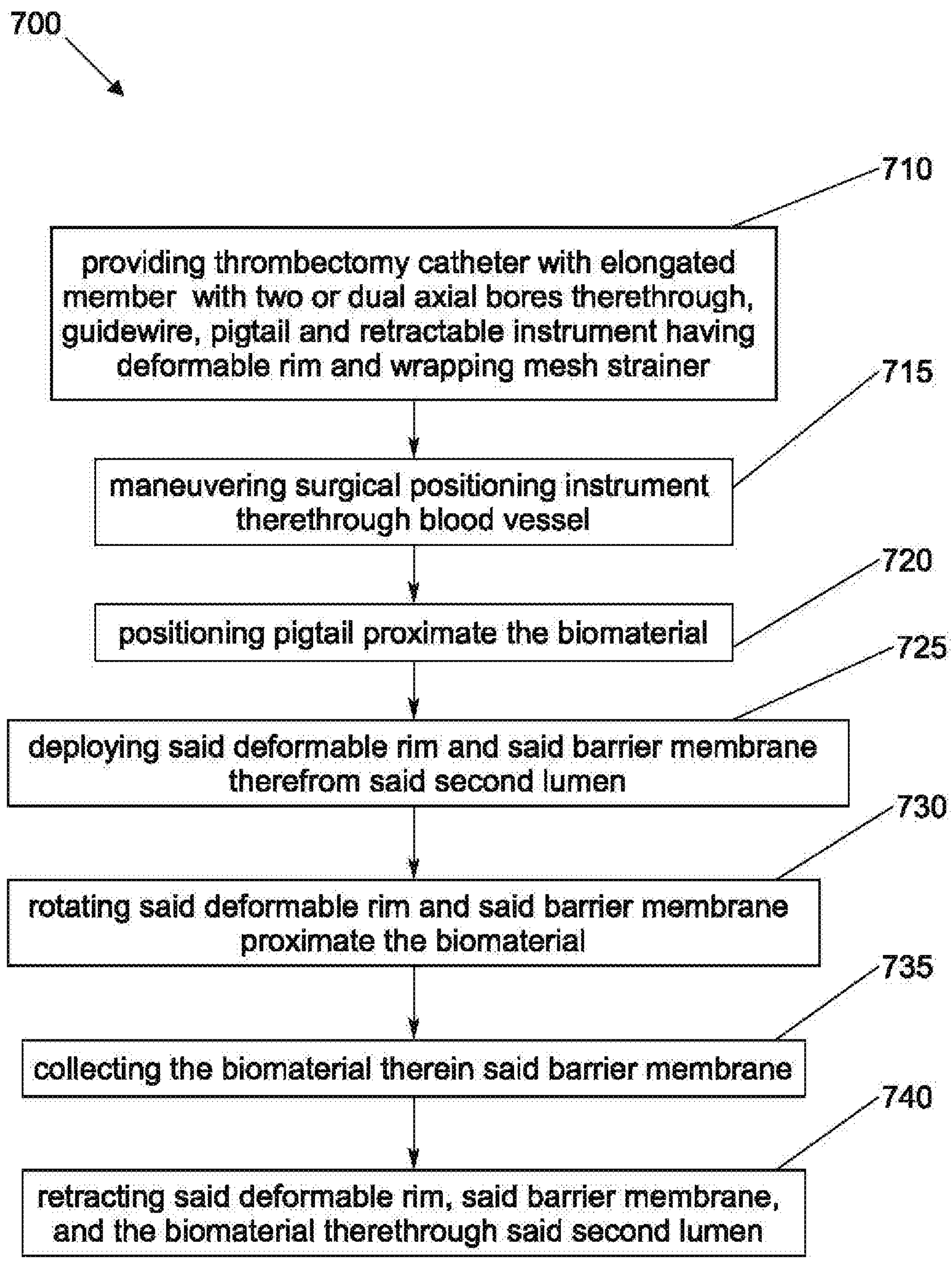
FIG. 7 is a flow diagram of a method deploying, using, and retrieving thrombectomy catheter of FIGS. 1-6 to remove undesirable material or debris from a vascular vessel.

Referring now to FIG. 7, there is illustrated a flow diagram 700 of utilizing surgical positioning instrument 10 and retractable instrument 60 to remove clots or the release of emboli, biomaterial, such as undesirable material or debris M from blood vessel V. In block or step 710, providing surgical positioning instrument 10 having elongated member 20 with two or dual axial bores therethrough, such as first lumen 31 and second lumen 32, and pigtail 50 on one end and integral retractable instrument 60 having deformable rim 67 and mesh strainer 63 as described above in FIGS. 1-6 including (collapsing deformable rim 67 and wrapping mesh strainer 63 therearound first member end 65 and insertion therein first instrument aperture 23 of second lumen 32) and (traversing first instrument aperture 23 (push/pull P1 of second member end 66) to second instrument aperture 25 of second lumen 32).

In block or step 715, manipulating or moving guidewire 40 (push/pull P1 of guidewire 40 or rotate R1 elongated member 20) to alter the position of pigtail 50 for a path or vessel guiding device to maneuver or advance surgical positioning instrument 10 therethrough blood vessel V, turn, fork or other vascular maneuverability and positioning pigtail 50 proximate material or debris M.

In block or step 720, deploying retractable instrument 60 via expanding deployed deformable rim 67 with mesh strainer 63 after passing therethrough second instrument aperture 25 to a position proximate pigtail 50 (deploying deformable rim 67 and mesh strainer 63 therefrom second lumen 32). When deployed first deformable section 61 and second deformable section 62 of deformable rim 67 expands back to a non-compressed position.

In block or step 730, rotating deformable rim 67 and mesh strainer 63 proximate material or debris M via rotating second member end 66 of retractable instrument 60, rotation R3, results in rotation R4 of deformable rim 67 having rim inlet 69 and mesh strainer 63, which in turn causes expanded deformable rim 67 having rim inlet 69 and mesh strainer 63 of retractable instrument 60 to scoop up or collect or capture clots, plaque, emboli, thrombi (blood clots), fatty deposit, biomaterial, or other undesirable material or debris M from blood vessel V.

In block or step 730, rotating deformable rim 67 and mesh strainer 63 proximate material or debris M via rotating elongated catheter 20, rotation R1, results in rotation R2 of pigtail 50 which in turn results in rotation R4 of deformable rim 67 having rim inlet 69 and mesh strainer 63 due to abutting or contact therebetween pigtail 50 and deformable rim 67, which in turn causes deformable rim 67 having rim inlet 69 and mesh strainer 63 of retractable instrument 60 to scoop up or collect or capture clots, plaque, emboli, thrombi (blood clots), fatty deposit, biomaterial, or other undesirable material or debris M from blood vessel V.

In block or step 735, collecting material or debris M therein mesh strainer 63 via scooping up or collecting or capturing clots, plaque, emboli, thrombi (blood clots), fatty deposit, biomaterial, or other undesirable material or debris M from blood vessel V therein mesh strainer 63.

In block or step 740, retracting deformable rim 67, mesh strainer 63, and material or debris M therethrough second instrument aperture 25 of second lumen 32 via collapsing deformable rim 67 by push/pull P1 of second member end 66 to retrieve collapsing deformable rim 67 and mesh strainer 63 may be furled or wrapped therearound deformable rim 67 and/or first member end 65, and retractable instrument 60 with undesirable material or debris M may be pulled therethrough or entry therein second instrument aperture 25 and exit out first instrument aperture 23.

In block or step 745, repeating steps 715-740.

Figure 8:
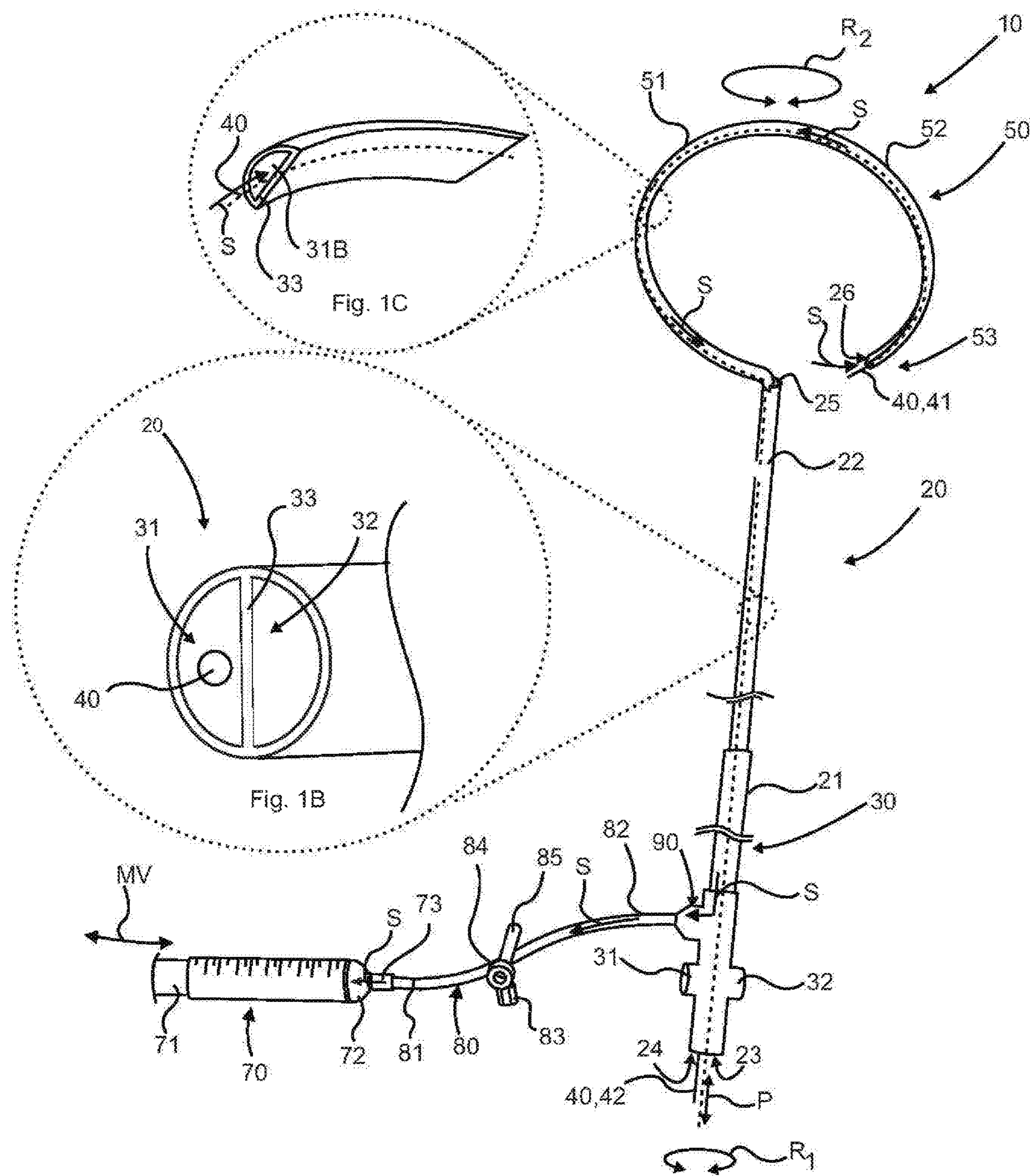
FIG. 8 is a top perspective view of an exemplary embodiment of a thrombectomy catheter with aspiration device.

Referring now to FIG. 8, by way of example, and not limitation, there is illustrated an example embodiment of a flexible surgical positioning instrument 10. Surgical positioning instrument 10 may include access hub or port, such as aspiration port 90 positioned proximate hand grip 36 or first catheter end 21. Aspiration port 90 may provide access, may be connected, in communication thereto first lumen 31 running the length thereof elongated catheter 20, pigtail lumen 31B of pigtail 50, and thereto pigtail end 53. Moreover, surgical positioning instrument 10 may include a side arm or conduit, such as aspiration tube 80 which may include a distal end, such as first tube end 81 and a proximate end, or second tube end 82. Second tube end 82 may be affixed or removeably affixed thereto aspiration port 90. Aspiration tube 80 may include three way stop cock valve 84 with cock bar 85. Cock bar 85 may be rotated (rotational) between open position for passage therethrough and for suction, diversion position to divert debris M to threaded port and cap 83, and closed position to seal second tube end 82. Furthermore, surgical positioning instrument 10 may include a suction, vacuum or negative pressure device, such as aspiration device 70. Aspiration device 70 may include a syringe having a housing or body such as syringe barrel 72, plunger 71 positioned therein and drawn or moved, such as as movement M therein syringe barrel 72, and adapter port 73 provides an exit or entrance thereto syringe barrel 72. Aspiration device 70 or more specifically adapter port 73 may be connected, in communication, or removeably connected thereto first tube end 81 preferably to perform aspiration, vacuum, or suction S therethrough aspiration tube 80, aspiration port 90, lumen 31 of elongated catheter 20, pigtail lumen 31B of pigtail 50, and therethrough pigtail end 53.

Figure 9:
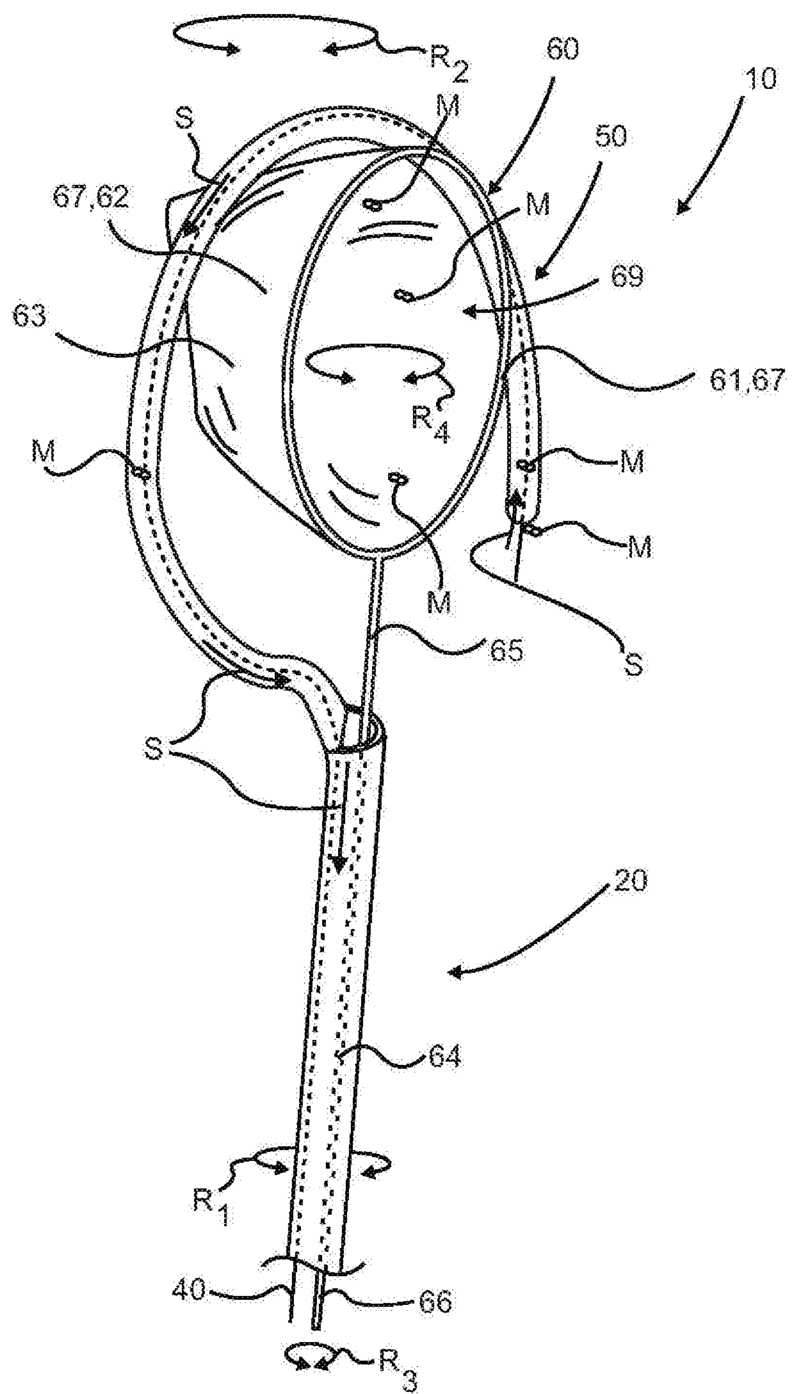
FIG. 9 is a top perspective view of an exemplary thrombectomy catheter of FIG. 8 with undesirable material being drawn therein lumen distal end.

Referring now to FIG. 9, by way of example, and not limitation, there is illustrated an example embodiment of pigtail 50 shown proximate clots, plaque, emboli, thrombi (blood clots), fatty deposit, biomaterial, or other undesirable material or debris M within blood vessel V. Moreover, aspiration or suction thereby aspiration device 70 preferably results in debris M being suctioned in or drawn or pulled (pulls/suctions) or collected or captured therein pigtail end 53. Furthermore with continued aspiration or suction (aspiration thrombectomy) thereby aspiration device 70 debris M may be pulled or traverse pigtail lumen 31B of pigtail 50, lumen 31 of elongated catheter 20, aspiration port 90, and aspiration tube 80, thereto aspiration device 70 whereby debris M has been removed therefrom blood vessel V.

It is contemplated herein that pigtail 50 may be in an extended configuration as shown in FIG. 2 rather than in a curled configuration as shown in FIG. 5 during aspiration or suction (aspiration thrombectomy) of debris M.

Figure 10:
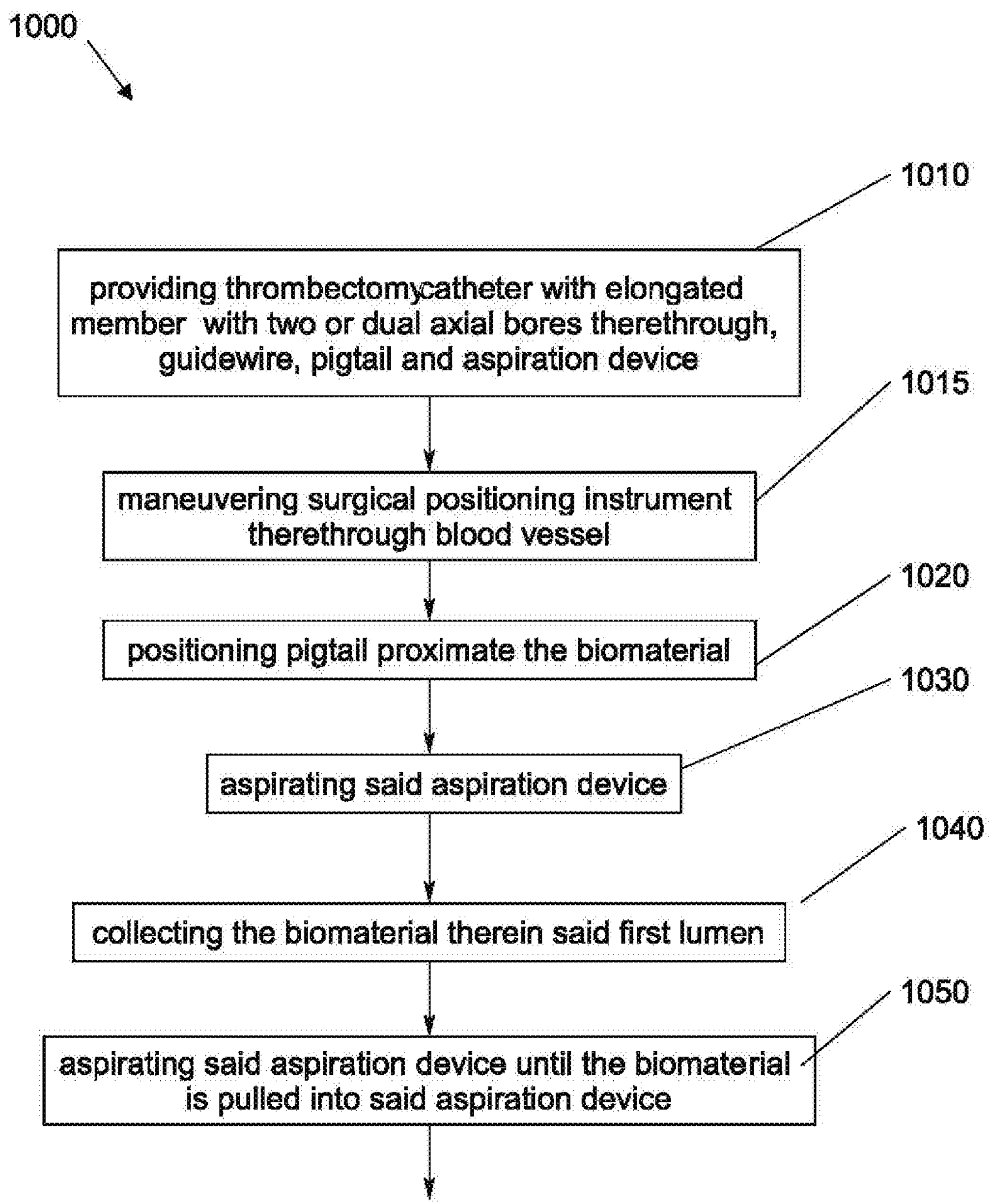
FIG. 10 is a flow diagram of a method deploying, using, and retrieving thrombectomy catheter of FIGS. 1-6 and 8-9 to remove undesirable material or debris from a vascular vessel via aspiration.

Referring now to FIG. 10, there is illustrated a flow diagram 1000 of utilizing surgical positioning instrument 10 and retractable instrument 60 to remove clots or the release of emboli, biomaterial, such as undesirable material or debris M from blood vessel V via aspiration or suction. In block or step 1010, providing surgical positioning instrument 10 having elongated member 20 with two or dual axial bores therethrough, such as first lumen 31 and second lumen 32, and pigtail 50 on one end and aspiration port 90, aspiration tube 80, and aspiration device 70 as described above in FIGS. 8-9.

In block or step 1015, manipulating or moving first catheter end 21 to alter the position of pigtail 50 for a path or vessel guiding device to maneuver or advance surgical positioning instrument 10 therethrough blood vessel V, turn, fork or other vascular maneuverability and positioning pigtail 50 proximate material or debris M, block or step 1020.

In block or step 1030, operating aspiration device 70 (aspirating or suctioning) for collecting, capturing, debris M therein pigtail end 53. Furthermore with continued aspiration or suction step 1040 (aspiration thrombectomy) thereby aspiration device 70 debris M may be pulled or traverse pigtail lumen 31B of pigtail 50, lumen 31 of elongated catheter 20, aspiration port 90, and aspiration tube 80, thereto aspiration device 70 step 1050 whereby debris M has been removed therefrom blood vessel V.

The foregoing description and drawings comprise illustrative embodiments of the present disclosure. Having thus described exemplary embodiments, it should be noted by those ordinarily skilled in the art that the within disclosures are exemplary only, and that various other alternatives, adaptations, and modifications may be made within the scope of the present disclosure. Merely listing or numbering the steps of a method in a certain order does not constitute any limitation on the order of the steps of that method. Many modifications and other embodiments of the disclosure will come to mind to one ordinarily skilled in the art to which this disclosure pertains having the benefit of the teachings presented in the foregoing descriptions and the associated drawings. Although specific terms may be employed herein, they are used in a generic and descriptive sense only and not for purposes of limitation. Moreover, the present disclosure has been described in detail, it should be understood that various changes, substitutions and alterations can be made thereto without departing from the spirit and scope of the disclosure as defined by the appended claims. Accordingly, the present disclosure is not limited to the specific embodiments illustrated herein, but is limited only by the following claims.

What is claimed is:

1. A remotely operated surgical device to traverse within a patient's vessel to a thrombus located therein, said surgical device comprising:

a flexible positioning instrument having an elongated catheter with a dual lumen bore therein extending from a first catheter end to a second catheter end, said dual lumen bore having a first lumen and a second lumen, and a flexible pigtail extending therefrom said second catheter end, said first lumen extends therethrough said elongated catheter and said flexible pigtail configured as a loop having a pigtail end that loops back to a position proximate said second catheter end, said pigtail end having a guidewire exit aperture, said second lumen extends therethrough said elongated catheter from said first catheter end therethrough said second catheter end to an instrument exit aperture proximate said second catheter end;

a guidewire extendable therethrough said first lumen of said elongated catheter and said flexible pigtail, and extendable therefrom said guidewire exit aperture, said guidewire extends through said flexible pigtail to straighten said flexible pigtail upon passage therethrough to enable said second catheter end and said flexible pigtail to traverse within the patient's vessel to the thrombus;

a retractable instrument having a proximal member and a distal member coupled to said proximal member, said distal member having a deformable circular rim and a barrier membrane affixed thereto, said deformable circular rim extendable therethrough said instrument exit aperture to expand said deformable circular rim to deploy said barrier membrane, wherein rotation of said first catheter end of said elongated catheter rotates said flexible pigtail, said flexible pigtail rotates said deformable circular rim and said barrier membrane by contact with said flexible pigtail to capture the thrombus therein said barrier membrane; and an aspiration device connected thereto said first lumen and configured to create a vacuum therein said first lumen of said elongated catheter and said flexible pigtail.

2. The remotely operated surgical device of claim 1, further comprising a guidewire entrance aperture positioned proximate said first catheter end and a guidewire exit aperture positioned proximate said pigtail end of said flexible pigtail.

3. The remotely operated surgical device of claim 1, wherein a rotation of said elongated catheter results in said rotation of said flexible pigtail.

4. The remotely operated surgical device of claim 3, wherein said flexible pigtail is configured to be disposed at a location within a patient's vessel.

5. The remotely operated surgical device of claim 1, further comprising a hand grip affixed thereto said first catheter end.

6. The remotely operated surgical device of claim 1, further comprising a first instrument aperture positioned proximate said first catheter end and a second instrument aperture positioned proximate said second catheter end.

7. The remotely operated surgical device of claim 1, wherein said flexible pigtail further comprises a pigtail lumen in communication with said first lumen.

8. The remotely operated surgical device of claim 7, further comprising an aspiration port positioned proximate said proximate said first catheter end, said aspiration port in communication with said first lumen.

9. The remotely operated surgical device of claim 8, further comprising an aspiration tube having a first tube end and a second tube end, said second tube end in communication with said aspiration port.

10. The remotely operated surgical device of claim 9, wherein said aspiration device is in communication with said first tube end.

11. The remotely operated surgical device of claim 10, wherein said aspiration device further comprises a syringe having a syringe barrel, a plunger positioned therein said syringe barrel, and adapter port exiting said syringe barrel.

12. The remotely operated surgical device of claim 10, wherein a rotation of said first catheter end is configured to result in said rotation of said pigtail end adjacent the thrombus therein.

13. The remotely operated surgical device of claim 12, wherein an aspiration therein said aspiration device creates an aspiration in said aspiration tube, said aspiration port, said first lumen, and said pigtail lumen to collect the thrombus therein.

14. The remotely operated surgical device of claim 13, wherein further aspiration therein said aspiration device suctions the thrombus through said pigtail lumen, said first lumen, said aspiration port, said aspiration tube, and into said aspiration device.

15. The remotely operated surgical device of claim 9, wherein said aspiration tube includes stop cock valve having a cock bar rotational between an open position, a diversion position, and a closed position.

16. The remotely operated surgical device of claim 1, further comprising an instrument entrance aperture connected to said second lumen and positioned proximate said first catheter end.

17. The remotely operated surgical device of claim 1, wherein said retractable instrument is configured to be withdrawn through said second lumen to remove the thrombus from the patient's vessel.

18. A method for removing a thrombus from a patient's vessel comprising the steps of:

providing a hand operated surgical device having a flexible positioning instrument, said flexible positioning instrument having an elongated catheter with a dual lumen bore therein extending from a first catheter end to a second catheter end, said dual lumen bore having a first lumen and a second lumen, and a flexible pigtail extending therefrom said second catheter end, said first lumen extends therethrough said elongated catheter and said flexible pigtail configured as a loop having a pigtail end that loops back to a position proximate said second catheter end, said pigtail end having a guidewire exit aperture, said second lumen extends therethrough said elongated catheter from said first catheter end therethrough said second catheter end to an instrument exit aperture proximate said second catheter end, a guidewire extendable therethrough said first lumen of said elongated catheter and said flexible pigtail and extendable therefrom said guidewire exit aperture, said guidewire extends through said flexible pigtail to straighten said flexible pigtail upon passage therethrough to enable said second catheter end and said flexible pigtail to traverse within the patient's vessel to the thrombus, a retractable instrument having a proximal member and a distal member coupled to said proximal member, said distal member having a deformable circular rim and a barrier membrane affixed thereto, said deformable circular rim extendable therethrough said instrument exit aperture to expand said deformable circular rim to deploy said barrier membrane, wherein rotation of said first catheter end of said elongated catheter rotates said flexible pigtail, said flexible pigtail rotates said deformable circular rim and said barrier membrane by contact with said flexible pigtail to break up capture the thrombus therein said barrier membrane and an aspiration device connected thereto said first lumen and configured to create a vacuum therein said first lumen of said elongated catheter and said flexible pigtail;

maneuvering said operated surgical device therethrough the patient's vessel;

positioning said flexible pigtail proximate the thrombus;

aspirating said aspiration device; and collecting the thrombus therein said first lumen.

19. The method of claim 18, further comprising the step of moving said guidewire therein said first lumen to straighten said flexible pigtail to an angle.

20. The method of claim 18, further comprising the step of rotating said first catheter end which rotates said flexible pigtail proximate the thrombus.

21. The method of claim 18, further comprising the step of moving said guidewire therein said first lumen to abut said flexible pigtail proximate the thrombus.

22. The method of claim 21, further comprising the step of aspirating the thrombus therethrough said first lumen to collect the thrombus therein said aspiration device.

* * * * *